United States Patent
Ito et al.

(10) Patent No.: US 11,666,237 B2
(45) Date of Patent: Jun. 6, 2023

(54) MEASUREMENT APPARATUS AND MEASUREMENT METHOD

(71) Applicant: SONY CORPORATION, Tokyo (JP)

(72) Inventors: Atsushi Ito, Kanagawa (JP); Kazunari Yoshifuji, Tokyo (JP)

(73) Assignee: SONY CORPORATION, Tokyo (JP)

( * ) Notice: Subject to any disclaimer, the term of this patent is extended or adjusted under 35 U.S.C. 154(b) by 353 days.

(21) Appl. No.: 16/757,294

(22) PCT Filed: Oct. 12, 2018

(86) PCT No.: PCT/JP2018/038044
§ 371 (c)(1),
(2) Date: Apr. 17, 2020

(87) PCT Pub. No.: WO2019/082688
PCT Pub. Date: May 2, 2019

(65) Prior Publication Data
US 2021/0186345 A1    Jun. 24, 2021

(30) Foreign Application Priority Data

Oct. 27, 2017    (JP) .............................. JP2017-207776

(51) Int. Cl.
| | | |
|---|---|---|
| *A61B 5/026* | (2006.01) | |
| *A61B 5/0285* | (2006.01) | |
| *G01F 1/66* | (2022.01) | |

(52) U.S. Cl.
CPC .......... *A61B 5/0261* (2013.01); *A61B 5/0285* (2013.01); *G01F 1/66* (2013.01)

(58) Field of Classification Search
CPC ... A61B 5/0261; A61B 5/0285; A61B 5/7203; A61B 5/7225; A61B 5/7239; A61B 5/7257; A61B 5/02; G01F 1/66; G01F 1/663; G01F 1/661
See application file for complete search history.

(56) References Cited

U.S. PATENT DOCUMENTS

| | | | | |
|---|---|---|---|---|
| 4,109,647 A | * | 8/1978 | Stern ...................... | G01P 3/36 356/28 |
| 4,516,432 A | | 5/1985 | Hironaga et al. | |

(Continued)

FOREIGN PATENT DOCUMENTS

| | | |
|---|---|---|
| DE | 69119296 T2 | 11/1996 |
| EP | 0458275 A2 | 11/1991 |

(Continued)

OTHER PUBLICATIONS

International Search Report and Written Opinion of PCT Application No. PCT/JP2018/038044, dated Dec. 11, 2018, 11 pages of ISRWO.

*Primary Examiner* — Jason M Sims
*Assistant Examiner* — Abid A Mustansir
(74) *Attorney, Agent, or Firm* — Chip Law Group

(57) ABSTRACT

The present technology relates to a measurement apparatus and a measurement method that realize reduction in power consumption while at the same time ensuring reduction in cost. Provided is a measurement apparatus that includes a light source, a light reception section, and a measurement section. The light source emits at least partially coherent light. The light reception section receives the light emitted from the light source by way of a measurement target and detects a signal proportional to the received light. The measurement section measures the number of oscillations included in the signal detected by the light reception section within a certain time period. For example, the present technology can be applied to a measurement apparatus measuring a blood flow of a human body.

9 Claims, 10 Drawing Sheets

(56) References Cited

U.S. PATENT DOCUMENTS

| | | | |
|---|---|---|---|
| 5,005,144 A | 4/1991 | Nakajima et al. | |
| 5,179,418 A | 1/1993 | Takamiya et al. | |
| 5,735,799 A * | 4/1998 | Baba | A61B 5/02108 600/500 |
| 6,475,153 B1 * | 11/2002 | Khair | A61B 5/026 600/485 |
| 2004/0145750 A1 | 7/2004 | Lin et al. | |
| 2009/0209871 A1 * | 8/2009 | Ueki | A61B 5/0261 600/504 |
| 2010/0298728 A1 * | 11/2010 | Addison | A61B 5/726 600/504 |
| 2013/0079657 A1 * | 3/2013 | Ochs | A61B 5/7235 600/529 |
| 2018/0156660 A1 * | 6/2018 | Turgeon | G09G 5/10 |
| 2018/0296168 A1 * | 10/2018 | Rice | A61B 5/7278 |

FOREIGN PATENT DOCUMENTS

| | | |
|---|---|---|
| JP | 54-028670 A | 3/1979 |
| JP | 62-076915 A | 4/1987 |
| JP | 01-233371 A | 9/1989 |
| JP | 02-203838 A | 8/1990 |
| JP | 02-236171 A | 9/1990 |
| JP | 04-025793 A | 1/1992 |
| JP | 05-015501 A | 1/1993 |
| JP | 2012-005598 A | 1/2012 |
| TW | 200410659 A | 7/2004 |

* cited by examiner

MEASUREMENT APPARATUS AND MEASUREMENT METHOD

CROSS REFERENCE TO RELATED APPLICATIONS

This application is a U.S. National Phase of International Patent Application No. PCT/JP2018/038044 filed on Oct. 12, 2018, which claims priority benefit of Japanese Patent Application No. JP 2017-207776 filed in the Japan Patent Office on Oct. 27, 2017. Each of the above-referenced applications is hereby incorporated herein by reference in its entirety.

TECHNICAL FIELD

The present technology relates to a measurement apparatus and a measurement method and particularly to a measurement apparatus and a measurement method that realize reduction in power consumption while at the same time ensuring reduction in cost.

BACKGROUND ART

A technology called a laser Doppler blood flow meter that non-invasively measures subcutaneous blood flow rate by shining coherent light onto a human skin and analyzing backscattered light thereof has been around, and measurement apparatuses using the technology have been available.

For example, PTL 1 discloses a technology that samples a reception intensity of scattered light, calculates a power value only at a specific frequency from the sampled reception intensity by using a DFT (Discrete Fourier Transform) formula, and obtains a pulse waveform or a pulse rate on the basis of a change in the power value over time.

CITATION LIST

Patent Literature

[PTL 1]
Japanese Patent Laid-Open No. 2012-005598

SUMMARY

Technical Problems

Incidentally, measurement apparatuses in the past have a DSP (Digital Signal Processor) or other IC (Integrated Circuit) to carry out a large number of calculations because of the need for calculations such as FFT (Fast Fourier Transform) and DFT, thus resulting in high cost and inhibiting power saving.

For this reason, a technology that realizes reduction in power consumption while at the same time ensuring reduction in cost has been sought after in a laser Doppler blood flow meter.

The present technology has been devised in light of the foregoing, and it is an object of the present technology to realize reduction in power consumption while at the same time ensuring reduction in cost.

Solution to Problems

A measurement apparatus of an aspect of the present technology includes a light source, a light reception section, and a measurement section. The light source emits at least partially coherent light. The light reception section receives the light emitted from the light source by way of a measurement target and detects a signal proportional to the received light. The measurement section measures the number of oscillations included in the signal detected by the light reception section within a certain time period.

A measurement method of an aspect of the present technology is a measurement method of a measurement apparatus for causing the measurement apparatus to receive light emitted from a light source that emits at least partially coherent light by way of a measurement target, detect a signal proportional to the received light, and measure the number of oscillations included in the detected signal within a certain time period.

In the measurement apparatus and the measurement method of an aspect of the present technology, light emitted from a light source that emits at least partially coherent light is received by way of a measurement target, a signal proportional to the received light is detected, and the number of oscillations included in the detected signal within a certain time period is measured.

It should be noted that the measurement apparatus of an aspect of the present technology may be an independent apparatus or an internal block included in an apparatus.

Advantageous Effects of Invention

An aspect of the present technology realizes reduction in power consumption while at the same time ensuring reduction in cost.

It should be noted that the effects described herein are not necessarily limited and may be any one of the effects described in the present disclosure.

DESCRIPTION OF EMBODIMENTS

Figure 1:
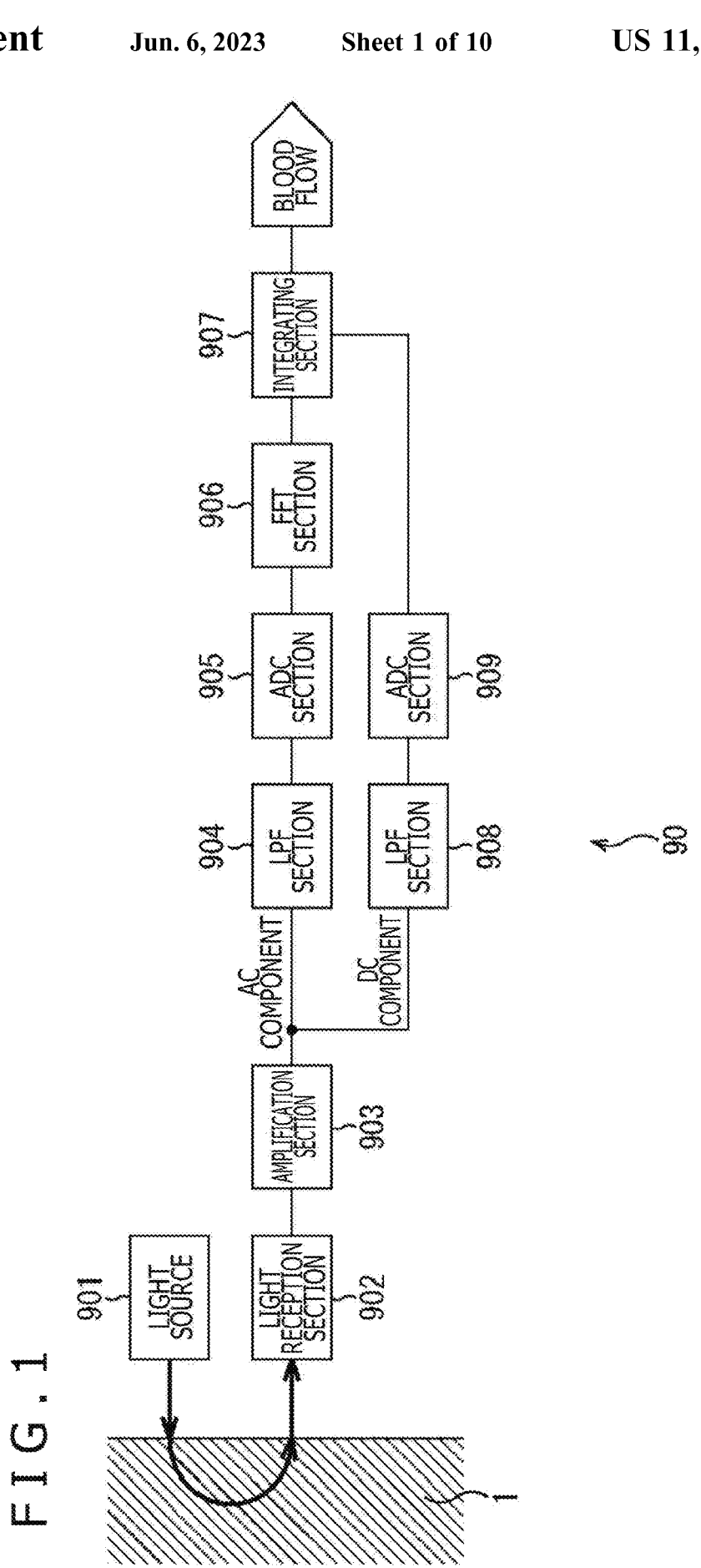
FIG. 1 is a block diagram illustrating a configuration of a common measurement apparatus.

A description will be given below of embodiments of the present technology with reference to drawings. It should be noted that the description will be given in the following order.

1. First Embodiment
2. Second Embodiment
3. Third Embodiment
4. Modification Example

1. First Embodiment

A brief description will be given first of a measurement principle of a measurement apparatus using a laser Doppler blood flow meter.

When light of an appropriate wavelength is shone on a human skin from outside, the majority thereof penetrates the skin, then is scattered by cell membranes and small organs, and is emitted again from the skin as a result as backscattered light. Of this scattered light, backscattered light produced by moving objects under the skin, and mainly by red corpuscles, is developing a slight change in wavelength due to Doppler effect.

If this change in frequency can be directly observed, a moving tissue velocity, i.e., a blood flow rate, can be measured. In reality, however, the number of light oscillations is extremely high or several hundreds of terahertz (THz), making it difficult to directly observe a Doppler shift of scattered light.

Incidentally, scattered light produced by stationary cells under the skin does not develop any Doppler shift. For this reason, if coherent light is shone, light from moving cells and that from stationary cells interfere with each other, producing, as a result, a beat signal as a beat.

This beat signal is of the order of a maximum of 20 kHz or so, making the signal readily observable with an ordinary and simple measurement apparatus. Therefore, a traveling velocity of red corpuscles can be found by measuring this beat signal.

Here, a common measurement technique converts a light beat signal into a digital signal with an ADC (Analog Digital Converter), accumulates data obtained as a result of the conversion for a certain time period, and then calculates the traveling velocity of blood by using formula (1) given below.

[Math. 1]

$$(\text{Blood flow}) = \frac{\int \omega P(\omega) d\omega}{\int P(\omega) d\omega} \quad (1)$$

In formula (1), $\omega$ represents an angular frequency of the beat signal, and $P(\omega)$ represents a power spectrum density of the beat signal.

However, in order to carry out such calculations in real time, digital data obtained by AD conversion is held for a certain time period, and then a power spectrum density is calculated, after which the blood flow is calculated by integration and division illustrated in formula (1).

As a specific example of this calculation, for example, in the case where a beat signal is sampled at 50 kHz and a power spectrum density is calculated from digital data collected from 1024 points, 20 ms are required for sampling. For this reason, data will be lost unless all calculations are completed within 20 ms.

As described above, a common laser Doppler blood flow meter achieves fast calculations by using a DSP (Digital Signal Processor). In this case, however, an expensive LSI (Large Scale Integration) is used, resulting in high cost and inhibiting power saving.

As a countermeasure, the above PTL 1 discloses a technology that, instead of calculating the power spectrum density, calculates the intensity of the beat signal only at a specific frequency, thus reducing the number of calculations and ensuring reduction in cost.

Incidentally, it is known that the beat signal frequency, proportional to the traveling velocity of red corpuscles, is expressed by a relational formula depicted below as formula (2).

[Math. 2]

$$\Delta\omega = |v| |k_i - k_s|, \quad (2)$$

In formula (2), v represents a particle velocity vector, $k_i$ represents an incident light vector, and $k_s$ represents a scattering vector.

It is clear from this formula (2) that there is a one-to-one proportional relationship between the particle velocity and the beat signal frequency and that one frequency corresponds to one particle velocity.

From such a relationship, in the case where the blood flow calculation technique according to the technology disclosed in the above PTL 1 is used, the calculation focuses only on a specific frequency. Therefore, the calculation corresponds to the measurement of the number of particles having a given velocity.

Here, a common laser Doppler blood flow meter calculates the blood flow from all frequencies (outputs a mean traveling velocity of moving particles). Therefore, it can be said that such a blood flow meter differs in measured physical quantity from the technology disclosed in the above PTL 1.

Also, the technology disclosed in the above PTL 1 does not calculate the power spectrum density. As a result, although a DSP may be unnecessary, additions and subtractions of data collected from 4096 points take place (e.g., recited in paragraphs [0041] and [0042] of PTL 1), resulting in a great deal of cost. For this reason, even if a DSP is unnecessary, it is difficult to realize a significant reduction in power consumption.

Further, as another problem, when the laser beam intensity changes due, for example, to temperature or deterioration, there is a case where standardization is performed with the laser beam intensity to ensure freedom from impact on the measured value during an integration process. In this case, an additional AD converter is required, thus resulting in increased cost.

Here, FIG. 1 illustrates a configuration of a common laser Doppler blood flow meter.

In FIG. 1, a measurement apparatus 90 includes a light source 901, a light reception section 902, an amplification section 903, an LPF section 904, an ADC section 905, an FFT section 906, an integrating section 907, an LPF section 908, and an ADC section 909.

The light source 901 includes an LD (Laser Diode) and a laser beam emitted from the light source 901 is shone on a human body 1, after which the laser beam is scattered by a skin tissue of the human body and received by the light reception section 902.

At this time, part of the light is scattered by particles (e.g., red corpuscles) moving in the human body 1 and so on, thus resulting in a Doppler shift. Then, the PD (Photodiode) provided in the light reception section 902 detects a random oscillation called a beat signal as a result of interference between Doppler-shifted light and non-Doppler-shifted light.

The signal detected by the light reception section 902 is amplified by the amplification section 903 and is output to the LPF section 904 and the LPF section 908.

The LPF section 904 is an LPF (Low Pass Filter) that gradually reduces frequency components of a signal (AC component signal) input from the amplification section 903 higher than a cutoff frequency and outputs a signal, obtained as a result, to the ADC section 905. It should be noted, however, that the signal input to the ADC section 905 is several tens of kHz in frequency. Therefore, a frequency slightly lower than half that frequency is the cutoff frequency of the LPF section 904.

The ADC section 905 converts the signal input from the LPF section 904 from analog to digital form (AD (Analog Digital) conversion) and outputs digital data, obtained as a result, to the FFT section 906. It should be noted that the ADC section 905 needs to extract only AC components. Therefore, an HPF (High Pass Filter) may be provided before or after the LPF section 904 or a BPF (Band Pass Filter) may be provided in place of the low pass filter (LPF) to cut DC components. At this time, the cutoff frequency of the band pass filter (BPF) is set to approximately several to several tens of Hz.

The FFT section 906 performs Fast Fourier transform (FFT) of the digital data (time domain signal) input from the ADC section 905 and outputs an FFT calculation result (frequency domain signal), obtained as a result, to the integrating section 907.

The LPF section 908 is a low pass filter (LPF) that gradually reduces frequency components of a signal (DC component signal) input from the amplification section 903 higher than the cutoff frequency and outputs a signal, obtained as a result, to the ADC section 909. It should be noted, however, that because only DC components are of interest, the cutoff frequency of the LPF section 908 is set to approximately several Hz, a frequency lower than the cutoff frequency of the LPF section 904.

The ADC section 909 performs AD conversion of the signal input from the LPF section 908 and outputs digital data (time domain signal), obtained as a result, to the integrating section 907.

The integrating section 907 receives, as inputs, an FFT computation result (frequency domain signal) from the FFT section 906 and digital data (time domain signal) from the ADC section 909. The integrating section 907 performs an integrating process on the basis of the FFT calculation result from the FFT section 906 and outputs a calculation result (measured value), obtained as a result, as a blood flow.

It should be noted, however, that when the intensity of the laser beam from the light source 901 changes due, for example, to temperature or deterioration, standardization is performed with the laser beam intensity by using the digital data from the ADC section 909 to ensure freedom from impact on the measured value during the integration process.

The measurement apparatus 90 is configured as described above.

Incidentally, as illustrated in the above formula (1), it is apparent that the blood flow is equal to calculation of a weighted mean of the power spectrum density of the beat signal. That is, finding the weighted mean of the power spectrum density is, in other words, synonymous to finding the mean frequency of the beat signal in which a variety of frequencies are superimposed.

Also, it is known that although a common laser Doppler blood flow meter can detect a relative change in blood flow, it does not indicate any absolute index of blood flow rate.

From this, it is reasonable to think that even if the mean frequency of the beat signal cannot be detected, the detection of a value proportional thereto can provide an equivalent result. That is, for example, the measurement of the total number of peaks appearing in the beat signal rather than the mean frequency of the beat signal provides an equivalent result.

From the above, the present technology measures an index (e.g., number of waves (number of oscillations) included in a detected signal within a certain time period) indicating the randomness of the beat signal along a time axis per unit time, thus acquiring an equivalent of the blood flow rate. A description will be given below of a configuration of a measurement apparatus to which the present technology is applied.

(Configuration of Measurement Apparatus of Present Technology)

Figure 2:
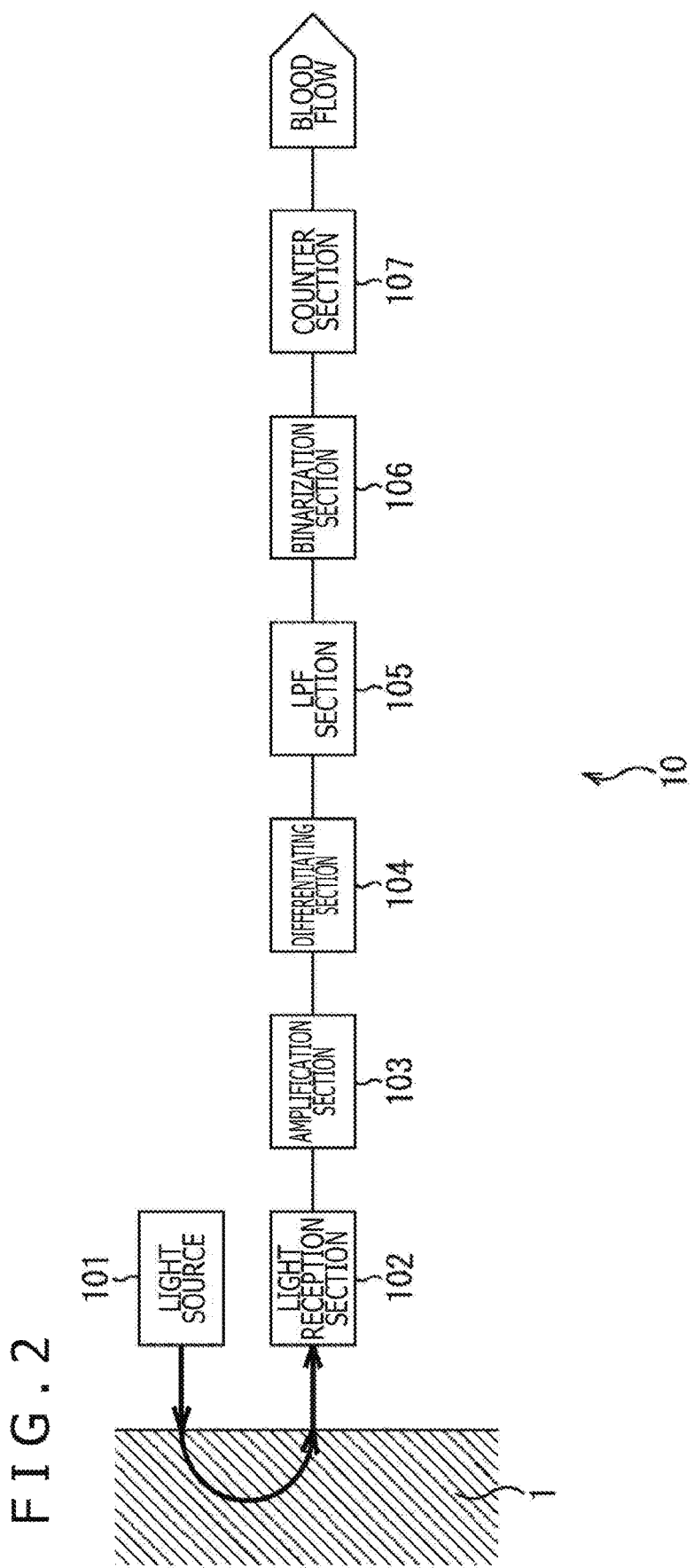
FIG. 2 is a block diagram illustrating a configuration of a measurement apparatus of a first embodiment.

FIG. 2 is a block diagram illustrating a configuration of a measurement apparatus of a first embodiment.

In FIG. 2, a measurement apparatus 10 includes a light source 101, a light reception section 102, an amplification section 103, a differentiating section 104, an LPF section 105, a binarization section 106, and a counter section 107.

The light source 101 is a light source that emits at least partially coherent light. For example, a DFB (Distributed Feedback) laser diode (LD), a VCSEL (Vertical Cavity Surface Emitting LASER), or other type of laser beam emitted in single mode can be used as the light source 101.

The light reception section 102 has a photoelectric conversion section that receives light that has passed through the human body 1 and converts the light into an electric signal. A photodiode (PD) that includes a silicon (Si) or other material can be used as this photoelectric conversion section.

Light emitted from the light source 101 is shone on the human body 1, scattered by a skin tissue of the human body 1, and received by the light reception section 102.

At this time, part of the light develops a Doppler shift as a result of scattering by moving particles (e.g., red corpuscles) and so on in the human body 1. Then, the PD (Photodiode) provided in the light reception section 102 develops interference between Doppler-shifted light and non-Doppler-shifted light, causing a random oscillation called a beat signal to be detected.

The light reception section 102 detects a signal proportional to the received light and outputs the detected signal to the amplification section 103. It should be noted that, although not illustrated, a current-voltage conversion section is provided between the light reception section 102 and the amplification section 103 to convert the signal output from the photodiode (PD) from a current into a voltage and outputs the voltage.

The amplification section 103 is an amplification circuit that amplifies the voltage to a degree that permits electrical processing and includes, for example, an operational amplifier and other parts.

The amplification section 103 amplifies the signal input from the light reception section 102 and outputs the amplified signal to the differentiating section 104. It should be noted that the amplification by the amplification section 103 may be performed simultaneously with the conversion performed by the above current-voltage conversion section.

The differentiating section 104 is a differentiating circuit that includes a first-order high pass filter (HPF) including an operational amplifier and other parts. Here, in the case of a first-order high pass filter (HPF) using an operational amplifier, a frequency lower than a cutoff frequency can be treated as a derivative. The differentiating section 104 performs a differentiation process on the signal input from the amplification section 103 and supplies the signal, obtained as a result, to the LPF section 105.

It should be noted that, although described in detail later, here it is preferred that a cutoff frequency should be set in such a manner as to reduce the amplitude of the low-frequency region to prevent low-frequency components from being measured with high intensity. For example, the cutoff frequency can be set to 100 Hz or higher. Further, it is preferred that the cutoff frequency should be set to 1000 Hz or higher.

The LPF section 105 is an LPF (Low Pass Filter) provided to prevent malfunction of the binarization section 106 and the counter section 107 provided at subsequent stages attributable to noise that may arise due to a variety of causes such as electrical and optical causes.

The LPF section 105 does not attenuate (hardly attenuates) frequency components of the signal input from the differentiating section 104 lower than the cutoff frequency, gradually reduces frequency components higher than the cutoff frequency, and outputs the signal, obtained as a result, to the binarization section 106.

It should be noted that, although described in detail later, the frequency distribution of beat signals generated in the human body 1 extends only up to approximately 10 kHz. Therefore, a frequency that cuts, for example, a frequency band beyond that frequency is set here as a cutoff frequency.

The binarization section 106 performs a binarization process on the signal input from the LPF section 105 and outputs the signal, obtained as a result, to the counter section 107.

It should be noted that, although described in detail later, this binarization process is performed to allow the number of extreme values of the signals to be measured by the counter section 107 provided at the subsequent stage. That is, although noise existing in high frequencies is removed by the LPF section 105 at the previous stage, impacts caused by noise with a small amplitude existing in low frequencies remains unremoved. Therefore, a binarization process is performed to eliminate the impacts caused by this noise.

Also, a hysteresis is desired to reduce this noise. A hysteresis width here is determined in accordance with the relationship with the amplification section 103, the amount of noise, and other factors. However, in the case where the input signal is amplified to 3 V, the hysteresis width is set to 0.1 V or more and desirably to between 0.3 and 0.7 V. It should be noted that, naturally, major signal components are no longer detectable as the hysteresis width increases, and, therefore, a suitable width should be set. However, this is left to each design.

The counter section 107 performs a counting process on the signal input from the binarization section 106 and outputs a measured value proportional to the count value, obtained as a result, as a blood flow.

It should be noted that, although described in detail later, this counting process is performed to count (measure) the number of extreme values existing in the detected signal within a certain time period.

There are no particular restrictions regarding the time period here. However, setting an extremely short time period results in so few extreme values to measure. On the other hand, setting an extremely long time period results in a low response to the change in blood flow. For this reason, it is desirable to set, for example, anywhere between 10 ms and 50 ms and suitably, anywhere between 15 ms and 30 ms as a time period. The reason for this is to properly measure approximately 1 Hz, a change in heartbeat caused by a blood flow.

The measurement apparatus 10 is configured as described above.

In the measurement apparatus 10 illustrated in FIG. 2, the differentiating section 104, the binarization section 106, and the counter section 107 are provided to measure extreme values in a signal so as to measure the randomness of a beat signal. A detailed description will be given here of a technique by which extreme values in a signal are measured, with reference to FIGS. 3 to 5.

Figure 3:
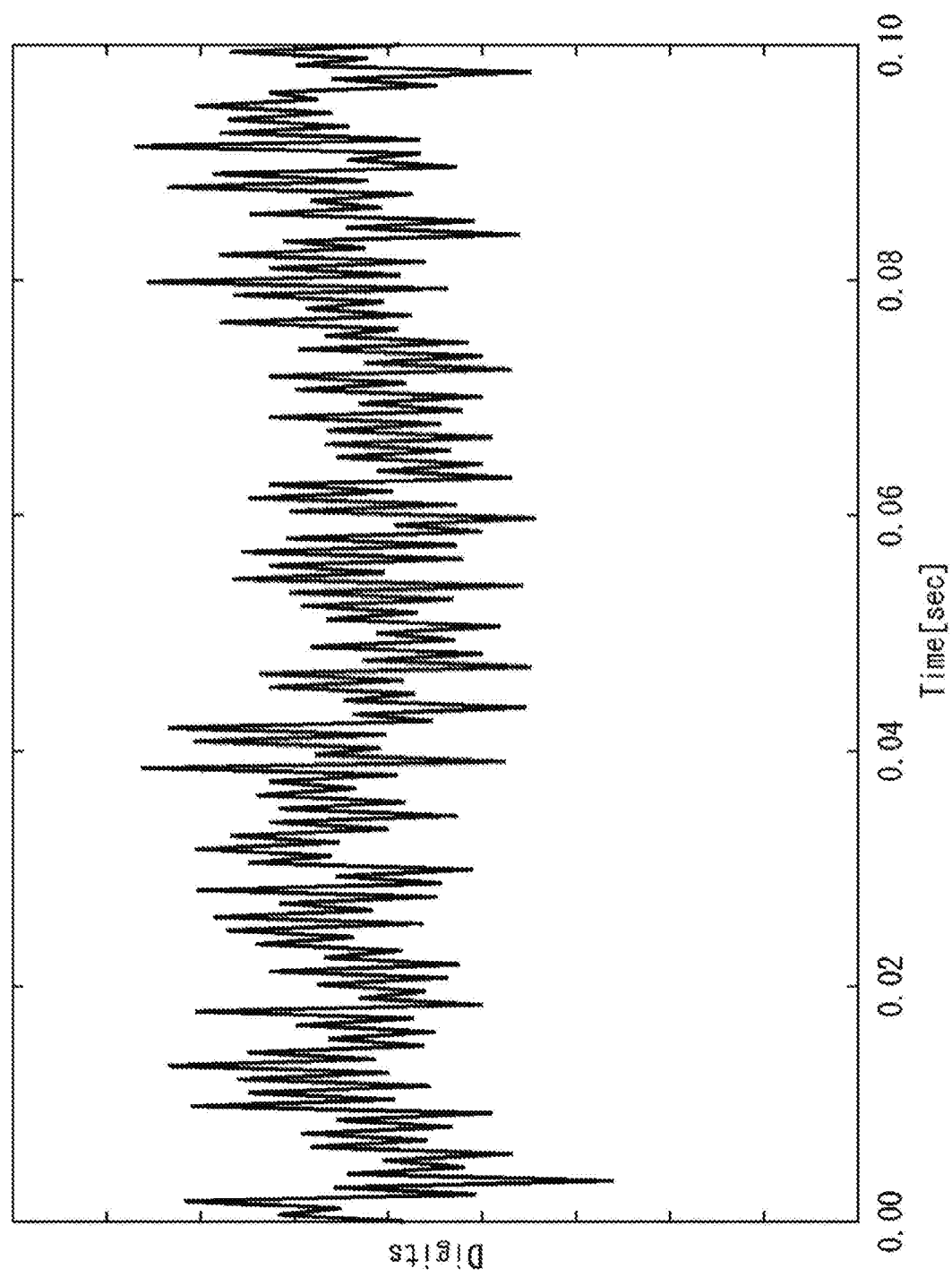
FIG. 3 is a diagram illustrating an example of a time domain of a beat signal.

FIG. 3 is a diagram illustrating an example of a time domain of a beat signal. It should be noted that, in FIG. 3, the vertical axis represents a detection result (Digits) of a signal detected by the photodiode (PD), and the horizontal axis represents time (in seconds).

Figure 4:
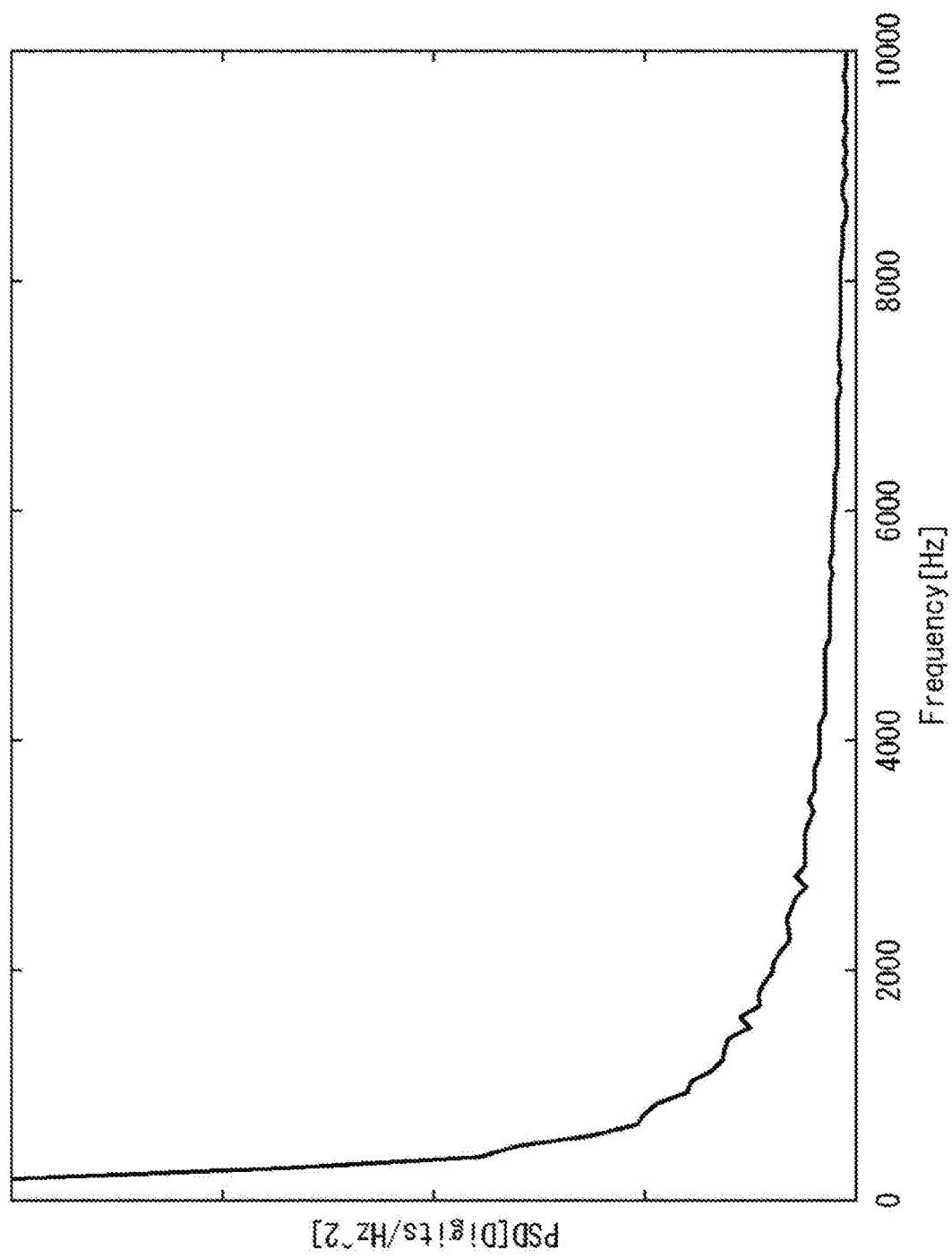
FIG. 4 is a diagram illustrating a frequency domain of a beat signal.

As illustrated in FIG. 3, the beat signal is an interference phenomenon detected by the photodiode (PD) and, therefore, is substantially random. FIG. 4 illustrates a frequency distribution of this beat signal by extracting a segment of the beat signal for a certain time period and performing Fourier conversion.

FIG. 4 illustrates a frequency domain of the beat signal. In FIG. 4, the vertical axis represents PSD (Power Spectrum Density), and the horizontal axis represents frequency (in Hz).

As illustrated in FIG. 4, the lower the frequency, the greater the amplitude of the beat signal, and the higher the frequency, the exponentially smaller the amplitude thereof. For this reason, in the case where the beat signal is binarized without differentiation, the binarization is performed by using only information regarding low frequencies with large amplitudes.

If the beat signal always has a constant frequency distribution, the overall frequency change can be represented simply by counting the number of waves of the low-frequency components. In reality, however, the mean frequency shifts to a high-frequency side with increase in blood flow rate, thus changing the shape of the frequency distribution itself.

Figure 5:
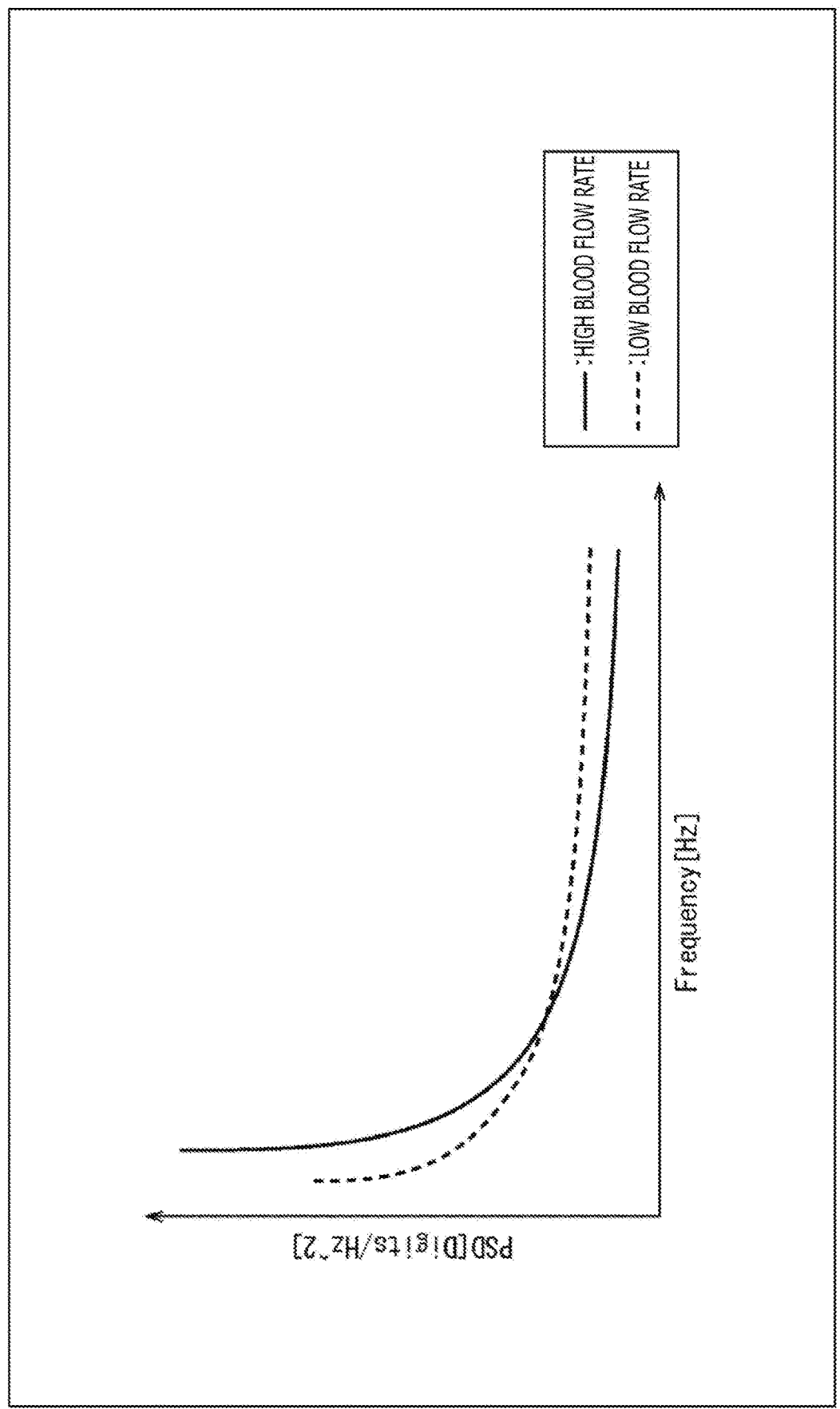
FIG. 5 is a diagram illustrating an example of a frequency domain of a beat signal proportional to a blood flow rate.

FIG. 5 illustrates an example of a frequency domain of a beat signal proportional to a blood flow rate. It should be noted that, in FIG. 5, the vertical and horizontal axes represent power spectrum density (PSD) and frequency, respectively as in FIG. 4.

FIG. 5 illustrates a power distribution for each unit frequency in the case where the blood flow rate is high and a power distribution for each unit frequency in the case where the blood flow rate is low. In FIG. 5, the power distribution in the case of a high blood flow rate has changed in shape of the frequency distribution itself because of a shifting of the mean frequency to a high frequency side as compared to the power distribution in the case of a low blood flow rate.

As described above, the mean frequency changes with change in blood flow rate, thus making it impossible to accurately represent the overall change in frequency simply by counting the number of waves of low-frequency components.

Also, in the case of measuring the human body 1, noise occurs as a result of the motion of the human body 1. However, this noise caused by the human motion is superimposed on low frequencies (e.g., frequencies approximately equal to or less than 100 Hz). This makes measurement error caused by human motion more likely.

For this reason, the differentiating section 104 is provided at the previous stage of the binarization section 106 that performs binarization in the preset technology. As described above, the differentiating section 104 is provided to obtain extreme values of the beat signal. This ensures that the binarization process with the binarization section 106 is less affected by the magnitude of the amplitude of the beat signal, causing binary high and low levels to change at each extreme value of the beat signal.

Thereafter, the number of changes in high and low levels of the signal for a certain time period is counted with the counter section 107, thus making it possible to count the number of extreme values during this time period.

This number of extreme values represents the total number of waves (number of oscillations) included during that time period. If the beat signal shifts to a high frequency side as a result of increase in blood flow rate, the number of waves (number of oscillations) will increase, thus causing the count value of the counter section 107 to increase. This count value itself is proportional to the weighted mean of the frequency. As a result, the count value is proportional to the blood flow rate.

Figure 6:
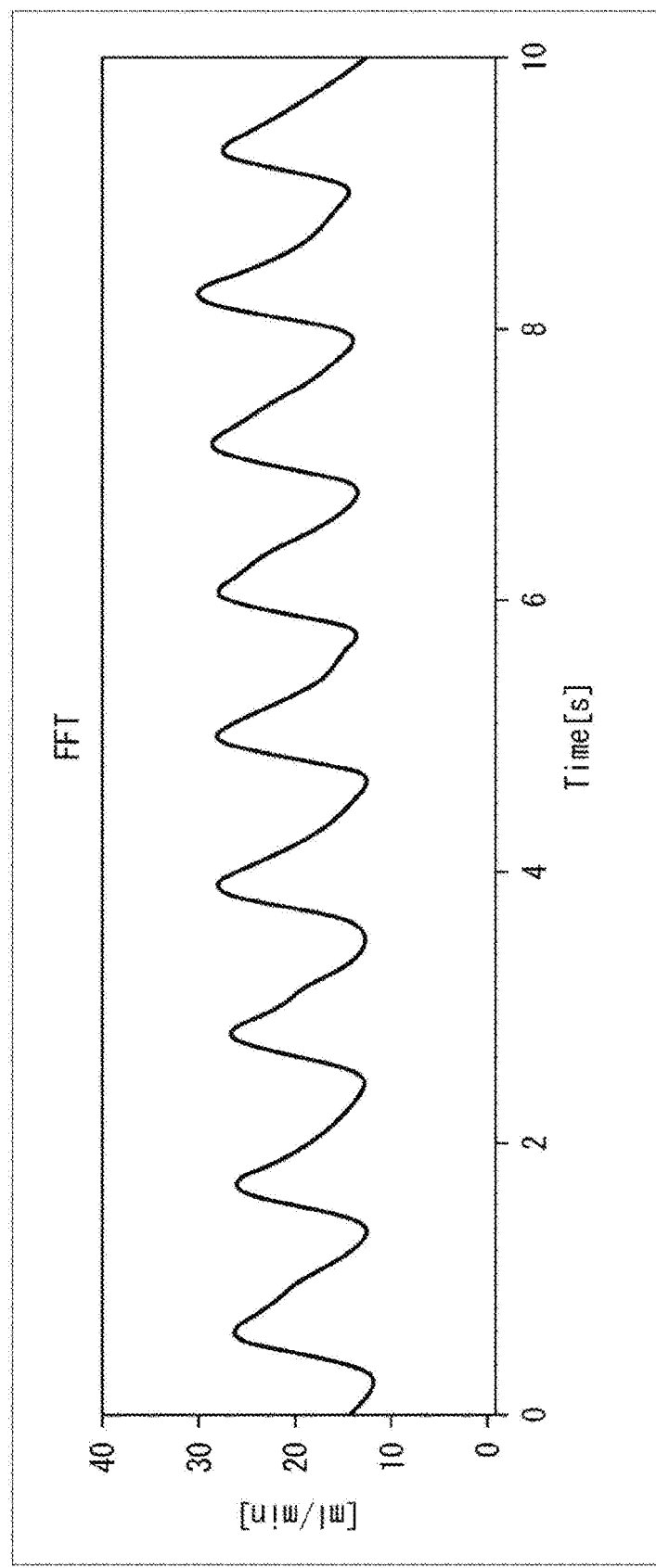
FIG. 6 is a diagram illustrating an example of a measurement result obtained by a common measurement apparatus.
Figure 7:
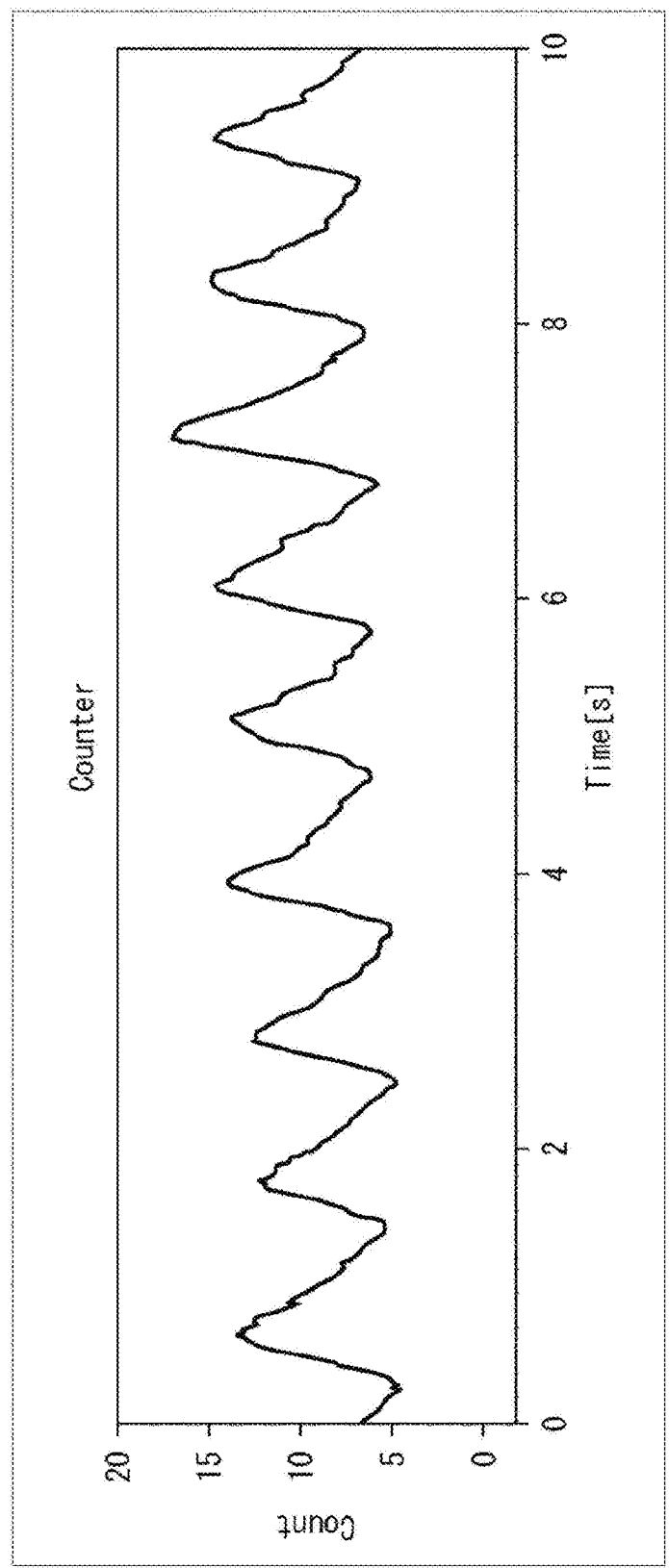
FIG. 7 is a diagram illustrating an example of a measurement result obtained by a measurement apparatus to which the present technology is applied.

Here, FIGS. 6 and 7 illustrate measurement results obtained simultaneously in the case where a common measurement apparatus (e.g., measurement apparatus 90 (FIG. 1)) is attached to the index finger of the left hand of a certain individual and where, further, the measurement apparatus 10 (FIG. 2) is attached to the middle finger of the left hand of the individual.

FIG. 6 illustrates an example of a measurement result obtained by a common measurement apparatus. It should be noted that, in FIG. 6, the vertical axis represents a measured value (in ml/min) obtained by Fast Fourier Transform (FFT) of the FFT section, and the horizontal axis represents time (in seconds).

On the other hand, FIG. 7 illustrates an example of a measurement result obtained by the measurement apparatus 10 (FIG. 2) to which the present technology is applied. It should be noted that, in FIG. 7, the vertical axis represents a count value (measured value) obtained by the counting process of the counter section 107, and the horizontal axis represents time (in seconds). Also, here the measured count value is subjected to smoothing to remove noise after the count value is measured, thus providing a smooth graph as illustrated in FIG. 7.

Then, the comparison between the measurement result of the common measurement apparatus illustrated in FIG. 6 and the measurement result of the measurement apparatus 10 illustrated in FIG. 7 depicts that although not completely the same because of the difference in measurement area, one on the index finger of the left hand and the other on the middle finger of the same hand, the two results are completely synchronous and nearly similar. That is, although the units along the vertical axes are different in FIGS. 6 and 7, the same unit, i.e., time (in seconds), is plotted along the horizontal axes, and the measurement results thereof are nearly similar waveforms.

As described above, the measurement apparatus 10 to which the present technology is applied measures the number of waves (number of oscillations) of a detected signal within a certain time period, thus eliminating the need for a step of measuring a frequency spectrum of the measured beat signal and finding a weighted mean, a step previously considered necessary for measurement apparatuses in the past, and providing comparable measurement results without using a high-performance calculator.

For this reason, the measurement apparatus 10 can remove, from its parts, an integrated circuit (e.g., LSI) such as DSP used in measurement apparatuses in the past. Further, in the measurement apparatus 10, extreme values are detected by the differentiating section 104 and the binarization section 106, and processing tasks are handled by using analog signals, thus making it possible to remove the AD converter (ADC) from its parts.

As described above, the measurement apparatus 10 to which the present technology is applied requires neither a DSP nor an AD converter, contributing to a cost reduction by the costs of the circuits removed and providing reduced power consumption. This keeps down power consumption while at the same time reducing costs.

Also, in measurement apparatuses in the past, increase in the number of components such as DSP and AD converter has translated into increase in measurement apparatus size. However, the measurement apparatus 10 to which the present technology is applied can be used without a DSP and an AD converter, thus ensuring downsizing of the measurement apparatus, as well. That is, the measurement apparatus 10 to which the present technology is applied ensures reduced cost, reduced power consumption, and downsizing.

Further, the measurement apparatus 90 (FIG. 1) described above separately detects a DC component for standardization to compensate for the change in laser beam intensity during calculation of the power spectrum density. However, the measurement apparatus 10 to which the present technology is applied simply counts the number of extreme values, making the apparatus substantially independent of the change in laser beam intensity.

For this reason, the measurement apparatus 10 does not need to measure a DC component and requires no DC component measurement circuit, thus ensuring low cost and low power consumption. In addition, there is no possibility that noise caused by DC component measurement may affect the measurement result, thus allowing for highly accurate measurement.

2. Second Embodiment (Configuration of Measurement Apparatus of Present Technology)

Figure 8:
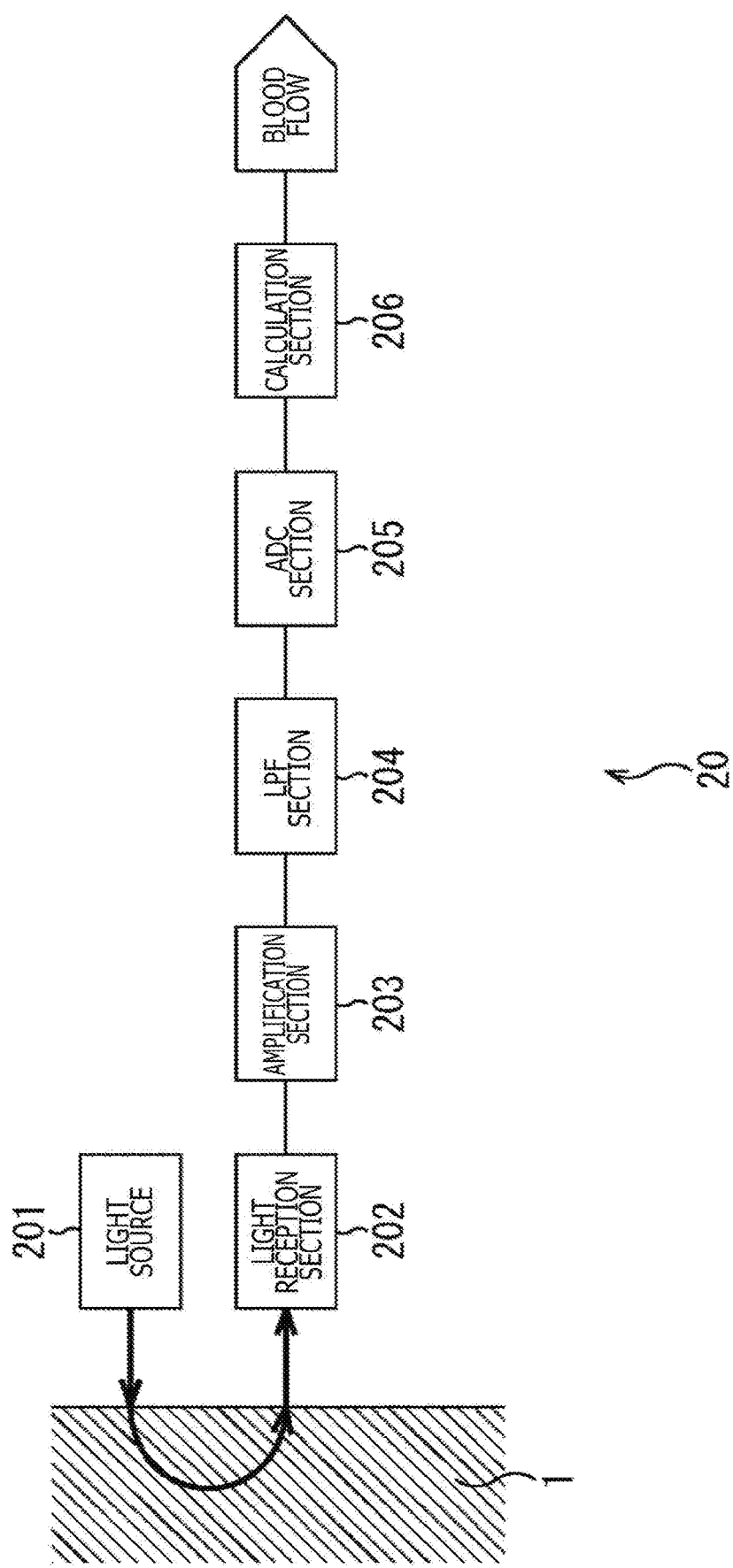
FIG. 8 is a block diagram illustrating an example of a configuration of a measurement apparatus of a second embodiment.

FIG. 8 is a block diagram illustrating an example of a configuration of a measurement apparatus of a second embodiment.

In FIG. 8, a measurement apparatus 20 includes a light source 201, a light reception section 202, an amplification section 203, an LPF section 204, an ADC section 205, and a calculation section 206.

The light source 201 and the light reception section 202 are configured in the same manner as the light source 101 and the light reception section 102 of FIG. 2. Light (coherent light) emitted from the light source 201 is shone on the human body 1, scattered by a skin tissue of the human body 1, and received by the light reception section 202.

At this time, part of the light is scattered by particles (e.g., red corpuscles) moving in the human body 1 and so on, thus resulting in a Doppler shift. As a result, the photodiode (PD) provided in the light reception section 202 detects a random oscillation because of interference between Doppler-shifted light and non-Doppler-shifted light.

The signal detected by the light reception section 202 is amplified by the amplification section 203 and is output to the LPF section 204.

The LPF section 204 is a low pass filter (LPF) that functions as an anti-aliasing filter (analog filter) during AD conversion at the subsequent stage.

The LPF section 204 does not attenuate (hardly attenuates) frequencies of the signal input from the amplification section 203 lower than the cutoff frequency, gradually reduces frequency components higher than the cutoff frequency, and outputs the signal, obtained as a result, to the ADC section 205.

The ADC section 205 performs AD conversion of the signal input from the LPF section 204 and outputs digital data, obtained as a result, to the calculation section 206. It should be noted that, for example, in the case where a sampling rate of the ADC section 205 is set to 50 kHz, the cutoff frequency of the LPF section 204 at the previous stage can be set to 20 kHz.

The calculation section 206 not only calculates a mean value over a certain time period by extracting a segment of the digital data input from the ADC section 205 but also successively processes each data point included in the extracted data and calculates the number of times that the values obtained by successive processing intersect the calculated mean value. The calculation section 206 outputs a measured value proportional to the calculated number of intersections as a blood flow.

That is, during calculation of the number of times that measurement points intersect a mean value over a certain time period by the calculation section 206, if, for example, the mean frequency of the beat signal increases as a result of increase in blood flow, the probability of the value obtained from each data point intersecting the mean value will increase. Therefore, a relative change in blood flow can also be detected by this technique.

As described above, the present technology measures an index indicating the randomness of the beat signal along the time axis per unit time, thus allowing for application of a variety of indexing techniques. As an example of such a technique, the calculation section 206 measures the number of times that measurement points intersect the mean value of the detected signal over a certain time period.

It should be noted that when measuring the blood flow, the calculation section 206 may calculate, while at the same time successively processing digital data (each data point included therein) input from the ADC section 205, calculate the number of times that an extreme value is reached. In this case, the operation of the measurement apparatus 10 of the first embodiment described above (e.g., operation of the differentiating section 104, the binarization section 106, and the counter section 107) has simply switched from analog to digital processing carried out by the measurement apparatus 20 (calculation section 206 thereof) of the second embodiment, and the two types of operation are equivalent.

It should be noted, however, that, regardless of the technique used for measuring the blood flow, the calculation section 206 should desirably have a dead zone such as hysteresis, for example, at the time of calculation of the number of intersections with the mean value or the number of extreme values to increase electrical and optical noise resistance.

The measurement apparatus 20 is configured as described above.

The measurement apparatus 20 to which the present technology is applied measures the number of waves (number of oscillations) in a detected signal within a certain time period, thus eliminating the need for a step of measuring a frequency spectrum of the measured beat signal and finding a weighted mean, a step previously considered necessary for measurement apparatuses in the past, and providing comparable measurement results without using a high-performance calculator.

Then, the measurement apparatus 20 requires no DCP or similar circuit, contributing to a cost reduction by the costs of the circuits removed and providing reduced power consumption. Also, in measurement apparatuses in the past, increase in the number of components such as DSP has translated into increase in measurement apparatus size. However, the measurement apparatus 20 can be used without a DSP or a similar circuit, thus ensuring downsizing of the measurement apparatus.

That is, the measurement apparatus 20 to which the present technology is applied ensures reduced cost, reduced power consumption, and downsizing.

3. Third Embodiment

Although the cases where the blood flow rate (blood flow) of the human body 1 is measured as a measurement target of the measurement apparatus 10 or the measurement apparatus 20 have been described in the above embodiments, the gist of the present technology is to measure a Doppler shift caused by the movement of scatterers with a simple electric circuit, and the measurement target is not limited to measurement of the blood flow rate of the human body 1.

As a measurement target, the measurement apparatus 10 or the measurement apparatus 20 is applicable, for example, to a case where the flow or flow rate is managed during processing of dairy products.

Specifically, for example, an ultrasonic Doppler current meter is known to be used as a current measurement method that does not block the passage. In the case where this configuration is used, it is necessary to provide a transmitter and a receiver. Also, it is difficult to measure a low current.

On the other hand, the measurement apparatus 10 or the measurement apparatus 20 to which the present technology is applied is low in cost and compact, allowing for installation at any location and measurement of the current at that position. Also, the measurement apparatus 10 or the measurement apparatus 20 is low in power consumption, allowing for measurement over an extended period of time.

It should be noted that although the step of managing dairy products was cited as an example, the present technology is capable of measuring a traveling speed of moving scatterers in a measurement target including a mixture of stationary scatterers with low light absorption and moving scatterers similarly with low light absorption, and the measurement target is not limited to dairy products. For example, not only human blood flow rate and dairy products but also a film feed rate during processing of scattering film are among examples of measurement targets, and the present technology can be also used to manage the film feed rate in question.

4. Modification Example

First Modification Example

Figure 9:
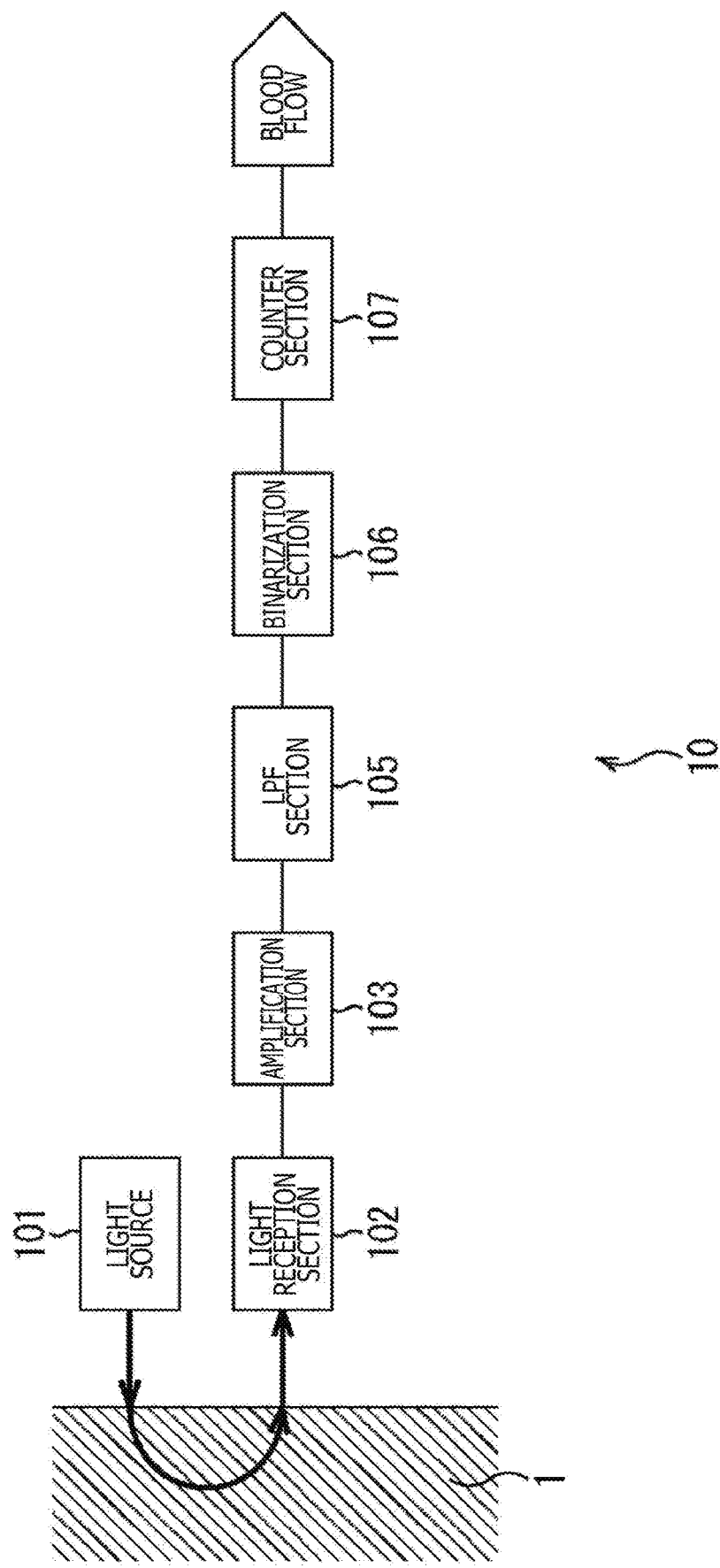
FIG. 9 is a block diagram illustrating a first modification example of the configuration of the measurement apparatus.

FIG. 9 is a block diagram illustrating a first modification example of the configuration of the measurement apparatus 10 illustrated in FIG. 2.

In FIG. 9, the measurement apparatus 10 differs from the configuration illustrated in FIG. 2 in that the differentiating section 104 provided between the amplification section 103 and the LPF 105 has been removed. That is, in FIG. 9, the LPF 105 does not attenuate (hardly attenuates) frequency components of the signal input from the amplification section 103 lower than the cutoff frequency, gradually reduces frequency components higher than the cutoff frequency, and outputs the signal, obtained as a result, to the binarization section 106.

As described above, the measurement apparatus 10 illustrated in FIG. 9 has no differentiating section 104. However, this configuration is effective in the case where the change in frequency distribution of the beat signal caused by the blood flow is small and, therefore, the overall frequency change can be represented simply by measuring the frequency with a relatively large amplitude. Adopting this configuration eliminates the need to provide a differentiating circuit, contributing to further reduction in number of parts as compared to measurement apparatuses in the past and ensuring further reduced cost, reduced power consumption, and downsizing.

It should be noted that, in the measurement apparatus 10 illustrated in FIG. 2, the counter section 107 may output, as a count value, a standardized count value obtained by division by the measurement time. This provides a reading of the counter section 107 per unit time, making the comparison possible even when the measurement time changes.

Also, the output value of the counter section 107 may be subjected to a smoothing process. Such a smoothing process provides a smoother output of the counter section 107. Further, although an example of counting the number of extreme values with the counter section 107 was illustrated above in the above description, the number of inflection points may be counted instead of the number of extreme values.

Further, in the measurement apparatus 10 illustrated in FIG. 2, there is no need to accommodate the light source 101 to the counter section 107 in the same housing. For example, the measurement apparatus 10 can include a sensor head section (sensor head apparatus) and a main body section (main body apparatus). The sensor head section has the light source 101, the light reception section 102, and the amplification section 103. The main body section has the differentiating section 104, the LPF section 105, the binarization section 106, and the counter section 107.

Similarly, in the measurement apparatus 20 illustrated in FIG. 8, there is no need to accommodate the light source 201 to the calculation section 206 in the same housing. For example, the measurement apparatus 20 can include a sensor head section (sensor head apparatus) and a (main body apparatus). The sensor head section has the light source 201, the light reception section 202, and the amplification section 203. The main body apparatus has the LPF section 204, the ADC section 205, the calculation section 206.

Second Modification Example

Figure 10:
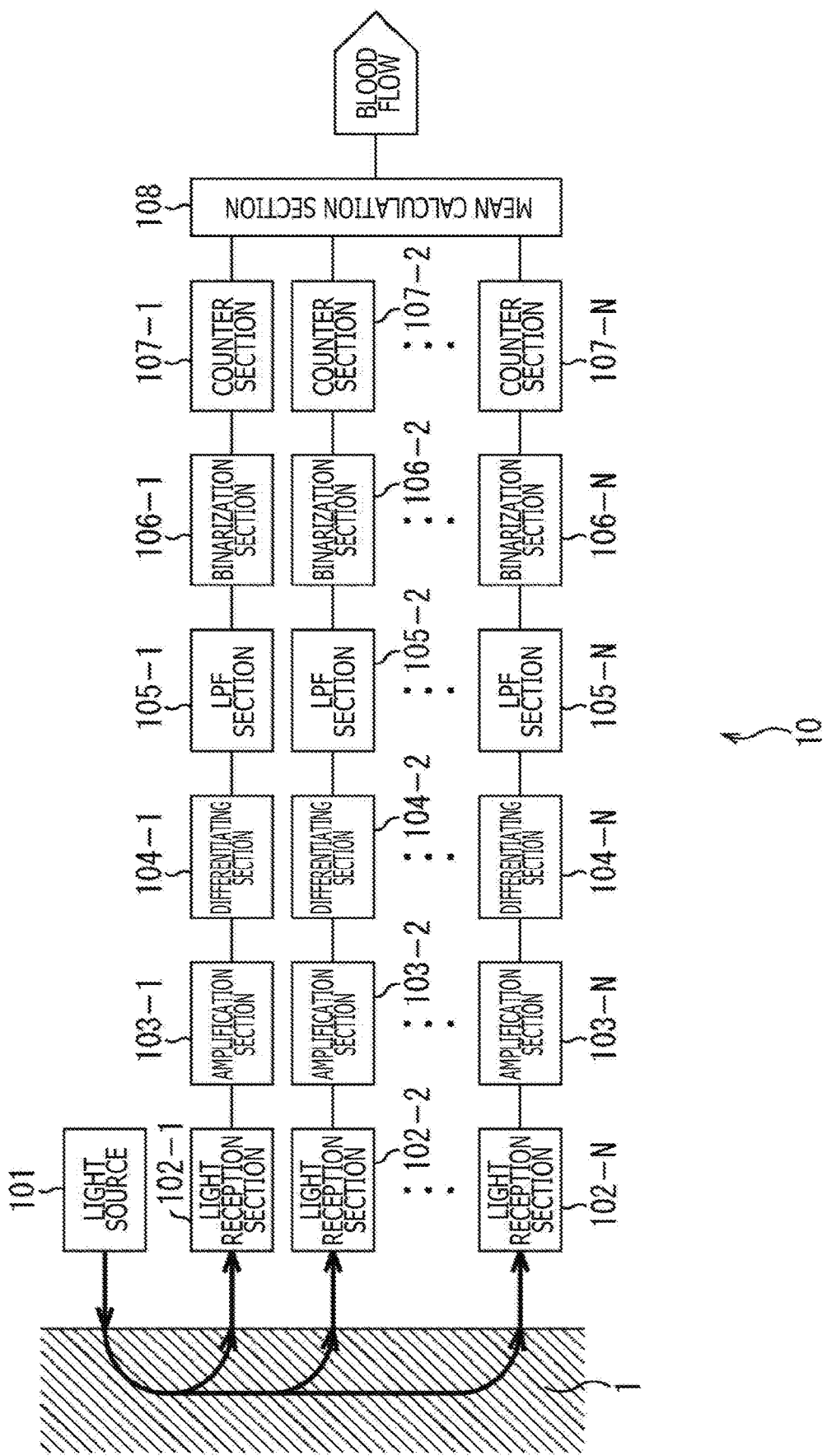
FIG. 10 is a block diagram illustrating a second modification example of the configuration of the measurement apparatus.

FIG. 10 is a block diagram illustrating a second modification example of the configuration of the measurement apparatus 10 illustrated in FIG. 2.

In FIG. 10, the measurement apparatus 10 has a plurality of lines that corresponds to a plurality of channels to the light source 101 as compared to the configuration illustrated in FIG. 2, and further, a mean calculation section 108 is provided to which an output value is input from each of these lines.

That is, in FIG. 10, the measurement apparatus 10 has, in addition to the light source 101, a first line that includes a light reception section 102-1 to a counter section 107-1, a second line that includes a light reception section 102-2 to a counter section 107-2, and so on up to an Nth line that includes a light reception section 102-N to a counter section 107-N, and the mean calculation section 108, where N is an integer equal to or larger than 1.

In the first line, the light reception section 102-1 to the counter section 107-1 process the signal proportional to the light received by the light reception section 102-1, allowing for the number of waves (number of oscillations) included in the detected signal within a certain time period to be measured and output to the mean calculation section 108.

In the second line, the light reception section 102-2 to the counter section 107-2 process the signal proportional to the light received by the light reception section 102-2, allowing for the number of waves (number of oscillations) included in a detected signal within a certain time period to be measured and output to the mean calculation section 108.

In the Nth line, the light reception section 102-N to the counter section 107-N process the signal proportional to the light received by the light reception section 102-N, allowing for the number of waves (number of oscillations) included in a detected signal within a certain time period to be measured and output to the mean calculation section 108.

The mean calculation section 108 calculates the mean of the measured values output from the first line (the counter section 107-1 thereof) to the Nth line (the counter section 107-N thereof) and outputs the mean as a blood flow.

As described above, there is a case where a plurality of channels is provided depending on the measurement technique used. However, the measurement apparatus 10 handles processing by using analog signals, thus making it unnecessary to provide an integrated circuit such as DSP for each channel and readily providing multiple channels.

It should be noted that embodiments of the present technology are not limited to those descried above and can be changed in various ways without departing from the gist of the present technology.

Also, the present technology can have the following configurations.

(1)

A measurement apparatus including:

a light source adapted to emit at least partially coherent light;

a light reception section adapted to receive the light emitted from the light source by way of a measurement target and detect a signal proportional to the received light; and a measurement section adapted to measure the number of oscillations included in the signal detected by the light reception section within a certain time period.

(2)

The measurement apparatus according to (1), in which the measurement section includes a counter that counts the number of extreme values of the signal.

(3)

The measurement apparatus according to (2), further including:

a binarization section adapted to perform a binarization process on the signal so as to count the number of extreme values.

(4)

The measurement apparatus according to (3), further including:

a differentiating section adapted to perform a differentiation process on the signal so as to acquire the extreme values, in which the binarization section performs the binarization process on the signal that has undergone the differentiation process.

(5)

The measurement apparatus according to (3) or (4), further including:

a frequency filter adapted to remove noise from the signal, in which the binarization section performs the binarization process on the signal from which noise has been removed by the frequency filter.

(6)

The measurement apparatus of according to any one of (3) to (5), in which the binarization section removes noise by setting up a hysteresis during the binarization process.

(7)

The measurement apparatus according to (1), in which the measurement section is a calculation section that calculates the number of times that measurement points intersect a mean value over the certain time period.

(8)

The measurement apparatus according to (7), further including:

an Analog Digital Converter section adapted to perform an Analog Digital conversion of the signal, in which the calculation section calculates a mean value of digital data, obtained by the Analog Digital conversion, over the certain time period and calculates the number of times the mean value and values obtained from respective data points included in the digital data intersect.

(9)

The measurement apparatus according to any one of (1) to (8), in which the light reception section and the measurement section are provided, one each for each channel, the measurement apparatus further including:

a mean calculation section adapted to calculate a mean value of measurement results of the respective channels.

(10)

The measurement apparatus according to any one of (1) to (9), in which the measurement target includes a human body, and the measurement section measures a blood flow in the human body.

(11)

A measurement method of a measurement apparatus for causing the measurement apparatus to:

receive light emitted from a light source that emits at least partially coherent light by way of a measurement target and detect a signal proportional to the received light; and measure the number of oscillations included in the signal detected within a certain time period.

REFERENCE SIGNS LIST

10 Measurement apparatus, 20 Measurement apparatus, 101 Light source, 102 Light reception section, 103 Amplification section, 104 Differentiating section, 105 LPF section, 106 Binarization section, 107 Counter section, 201 Light source, 202 Light reception section, 203 Amplification section, 204 LPF section, 205 ADC section, 206 Calculation section

The invention claimed is:

1. A measurement apparatus, comprising:

a light source configured to emit at least partially coherent light;

a photodiode configured to:

receive the partially coherent light emitted from the light source by way of a measurement target; and detect a signal proportional to the received partially coherent light; and circuitry configured to:

perform an analog to digital conversion of the signal to generate a digital data;

extract a segment of the digital data;

obtain value of respective data points on the extracted segment of the digital data;

calculate, based on the extracted segment, a mean value of the digital data;

calculate a number of times the mean value and the value of the respective data points intersects; and output a measured value of blood flow of the measurement target based on the number of times the mean value and the value of the respective data points intersects.

2. The measurement apparatus according to claim 1, further comprising a counter configured to count number of extreme values of the signal.

3. The measurement apparatus according to claim 2, wherein the circuitry is further configured to perform a binarization process on the signal to count the number of extreme values.

4. The measurement apparatus according to claim 3, further comprising:

a high-pass filter configured to perform a differentiation process on the signal to acquire the extreme values, wherein the circuitry is further configured to perform the binarization process on the signal after the differentiation process.

5. The measurement apparatus according to claim 3, further comprising:

a frequency filter adapted to remove noise from the signal, wherein the circuitry is further configured to perform the binarization process on the signal based on the removal of the noise by the frequency filter.

6. The measurement apparatus according to claim 5, wherein the circuitry is further configured to remove the noise based on setup of a hysteresis during the binarization process.

7. The measurement apparatus according to claim 1, wherein the measurement apparatus has a plurality of channels to the light source, a first channel of the plurality of channels includes the photodiode and the circuitry, and the circuitry is further configured calculate the mean value of measurement results of respective channels.

8. The measurement apparatus according to claim 1, wherein the measurement target includes a human body.

9. A measurement method, comprising:

in a measurement apparatus:

emitting, by a light source, at least partially coherent light;

receiving, by a photodiode, the partially coherent light emitted from the light source by way of a measurement target;

detecting a signal proportional to the received partially coherent light;

performing, by circuitry, an analog to digital conversion of the signal to form a digital data;

extracting, by the circuitry, a segment of the digital data;

obtaining, by the circuitry, value of respective data points on the extracted segment of the digital data;

calculating, by the circuitry, based on the extracted segment, a mean value of the digital data;

calculating, by the circuitry, a number of times the mean value and the value of the respective data points intersects; and outputting, by the circuitry, a measured value of blood flow of the measurement target based on the number of times the mean value and the value of the respective data points intersects.

\* \* \* \* \*